US011504036B2

United States Patent
Pang et al.

(10) Patent No.: US 11,504,036 B2
(45) Date of Patent: Nov. 22, 2022

(54) DRY ADHESIVE PATCH WITH MICRO-ABSORBENT HYBRID STRUCTURE CAPABLE OF CAPTURING AND CLEANLY-ADHERING BODY-FLUID AND MANUFACTURING METHOD THEREOF

(71) Applicant: Research & Business Foundation Sungkyunkwan University, Suwon-si (KR)

(72) Inventors: Chang Hyun Pang, Suwon-si (KR); Sang Yul Baik, Suwon-si (KR); Da Wan Kim, Suwon-si (KR); Ji Hyun Lee, Gunpo-si (KR)

(73) Assignee: Research & Business Foundation Sungkyunkwan University, Suwon-si (KR)

( * ) Notice: Subject to any disclaimer, the term of this patent is extended or adjusted under 35 U.S.C. 154(b) by 541 days.

(21) Appl. No.: 16/783,621

(22) Filed: Feb. 6, 2020

(65) Prior Publication Data
US 2020/0261001 A1    Aug. 20, 2020

(30) Foreign Application Priority Data
Feb. 14, 2019    (KR) .................. 10-2019-0017267

(51) Int. Cl.
*A61B 5/145* (2006.01)
*A61B 5/1477* (2006.01)
*A61B 5/00* (2006.01)

(52) U.S. Cl.
CPC ........ *A61B 5/1477* (2013.01); *A61B 5/14507* (2013.01); *A61B 5/6833* (2013.01)

(58) Field of Classification Search
CPC ............ A61B 5/14507; A61B 5/14517; A61B 5/1477; A61B 5/6833; C09J 7/00; C09J 2301/31; B81C 1/00111; B81B 2203/0361
See application file for complete search history.

(56) References Cited

U.S. PATENT DOCUMENTS

| 10,327,704 B2* | 6/2019 | Pang ................... A61F 13/0253 |
| 10,575,667 B2* | 3/2020 | Hulseman .......... A47G 19/2288 |
| 2014/0363610 A1* | 12/2014 | Sameoto ............... B29C 43/003 428/92 |

(Continued)

FOREIGN PATENT DOCUMENTS

| KR | 10-2016-0080080 | 7/2016 |
| KR | 10-1833821 | 3/2018 |

OTHER PUBLICATIONS

Baik S, Kim DW, Park Y, Lee TJ, Ho Bhang S, Pang C. A wet-tolerant adhesive patch inspired by protuberances in suction cups of octopi. Nature. Jun. 14, 2017;546(7658):396-400. doi: 10.1038/nature22382. PMID: 28617467. (Year: 2017).*

(Continued)

*Primary Examiner* — Eric J Messersmith
(74) *Attorney, Agent, or Firm* — NSIP Law

(57) ABSTRACT

Disclose is a dry adhesive patch comprising: a plurality of embossed pillars formed on a substrate; a hemi-spherical adsorbing cup defining a top portion of each pillar, wherein a hemi-spherical hole is defined in a top portion of the adsorbing cup and is exposed to an outside; and an annular extension extending radially from an outer perimeter of a distal end of each adsorbing cup.

13 Claims, 17 Drawing Sheets

Adhesive patch with diving beetle-inspired architectures for multidirectional, reversible attachment and sweat capture

(56) References Cited

U.S. PATENT DOCUMENTS

| | | | | |
|---|---|---|---|---|
| 2015/0159067 A1* | 6/2015 | Pesika | ............... | B81C 1/00103 |
| | | | | 264/129 |
| 2015/0329743 A1* | 11/2015 | Lu | ............................ | C09J 7/00 |
| | | | | 428/196 |
| 2015/0367380 A1* | 12/2015 | Kotov | ............... | B29C 37/0053 |
| | | | | 428/206 |
| 2016/0160097 A1* | 6/2016 | Waite | .................. | C07F 7/1804 |
| | | | | 526/279 |
| 2016/0206243 A1* | 7/2016 | Pang | ................. | A61B 5/6834 |

OTHER PUBLICATIONS

Bae WG, Kim D, Kwak MK, Ha L, Kang SM, Suh KY. Enhanced skin adhesive patch with modulus-tunable composite micropillars. Adv Healthc Mater. Jan. 2013;2(1):109-13. doi: 10.1002/adhm.201200098. Epub Aug. 13, 2012. PMID: 23184425. (Year: 2012).*

Kwak MK, Jeong HE, Suh KY. Rational design and enhanced biocompatibility of a dry adhesive medical skin patch. Adv Mater. Sep. 8, 2011;23(34):3949-53. doi: 10.1002/adma.201101694. Epub Jul. 28, 2011. PMID: 21796686. (Year: 2011).*

Babak Soltannia and Dan Sameoto. Strong, Reversible Underwater Adhesion via Gecko-Inspired Hydrophobic Fibers, ACS Applied Materials & Interfaces 2014 6 (24), 21995-22003 DOI: 10.1021/am5075375 (Year: 2014).*

* cited by examiner

[FIG. 1A]
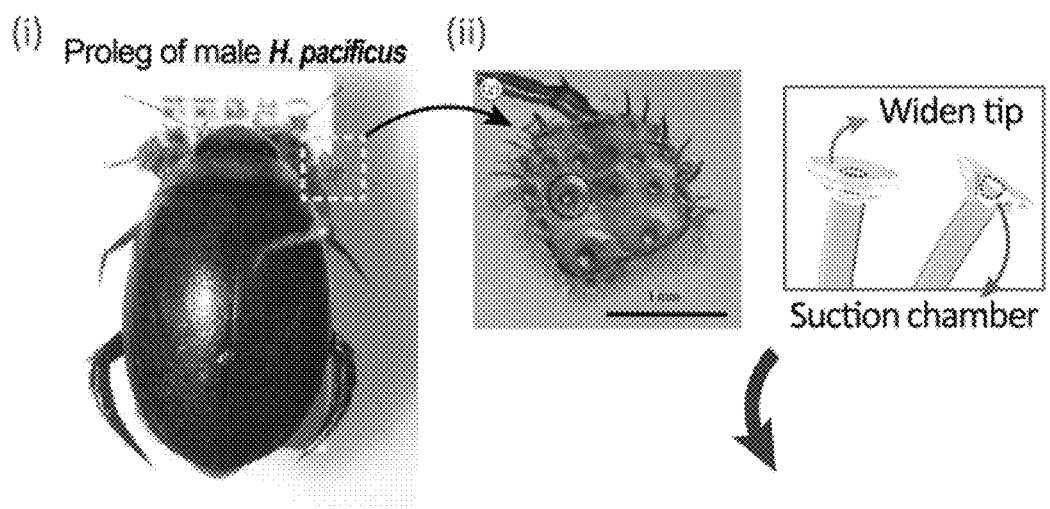
[FIG. 1B]
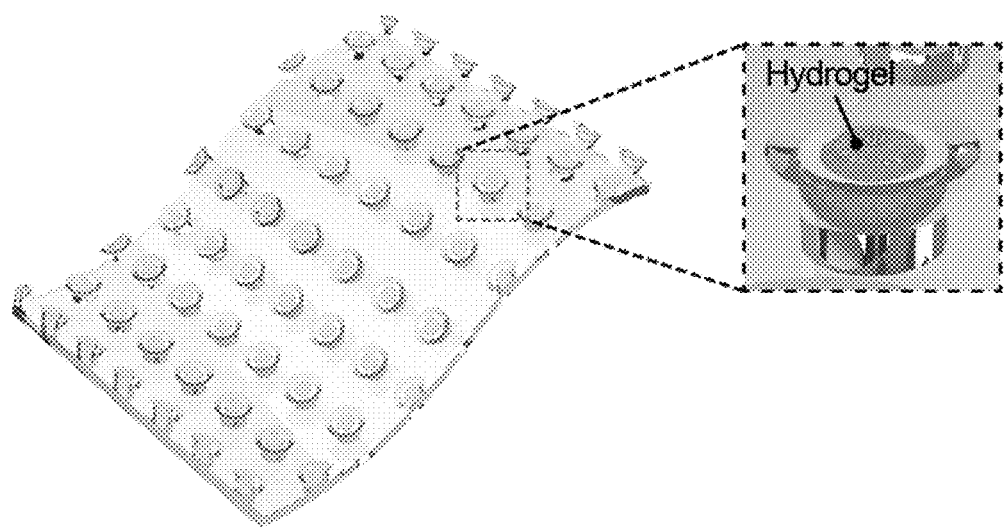
*Adhesive patch with diving beetle-inspired architectures for multidirectional, reversible attachment and sweat capture*

[FIG. 1C]
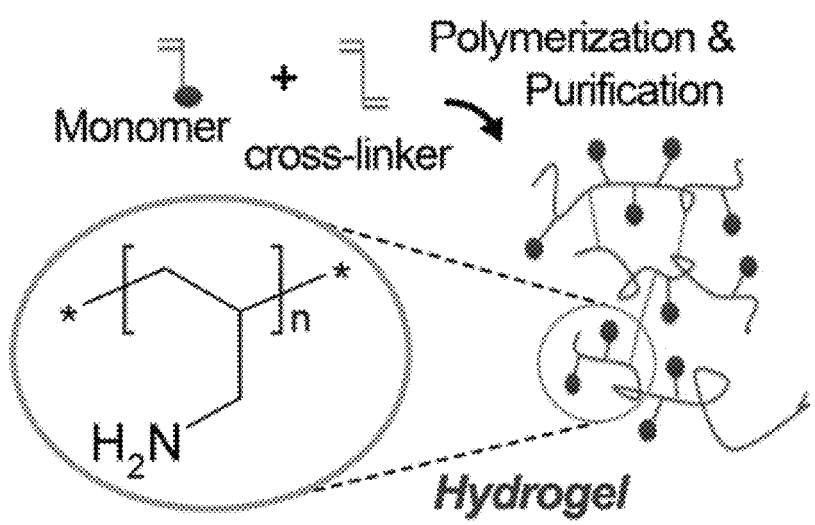
[FIG. 1D]
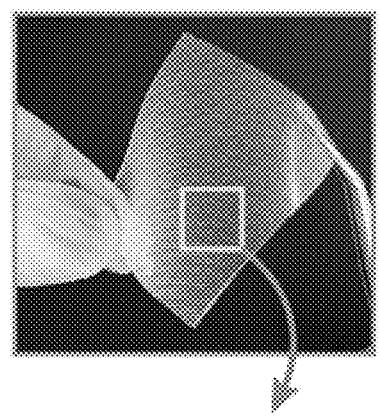

[FIG. 1E]
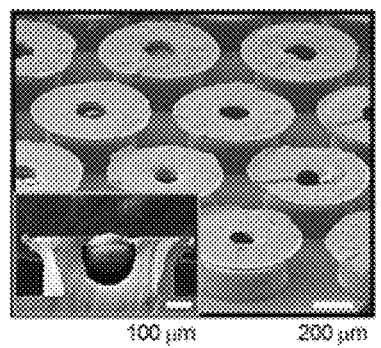
[FIG. 1F]
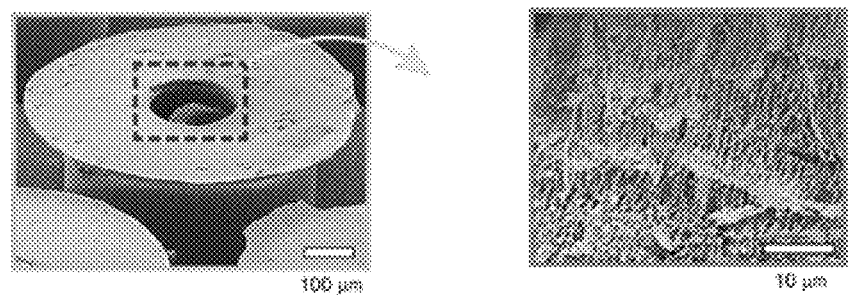

[FIG. 2A]
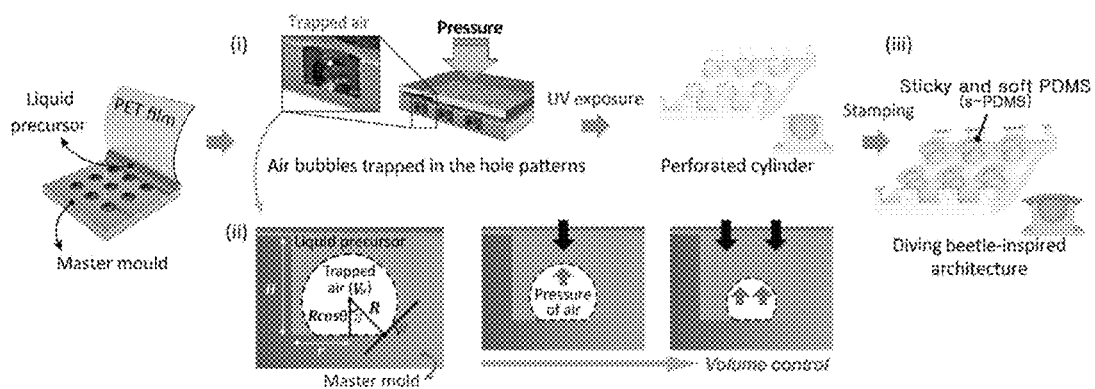
[FIG. 2B]
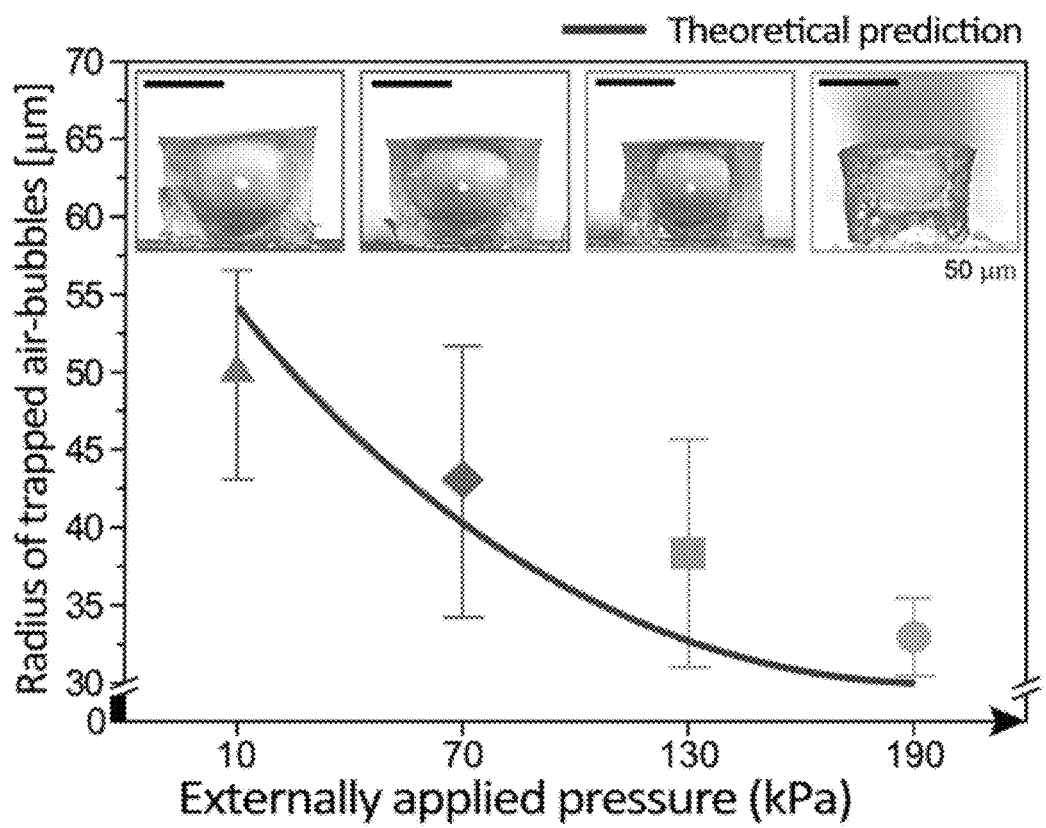

[FIG. 2C]
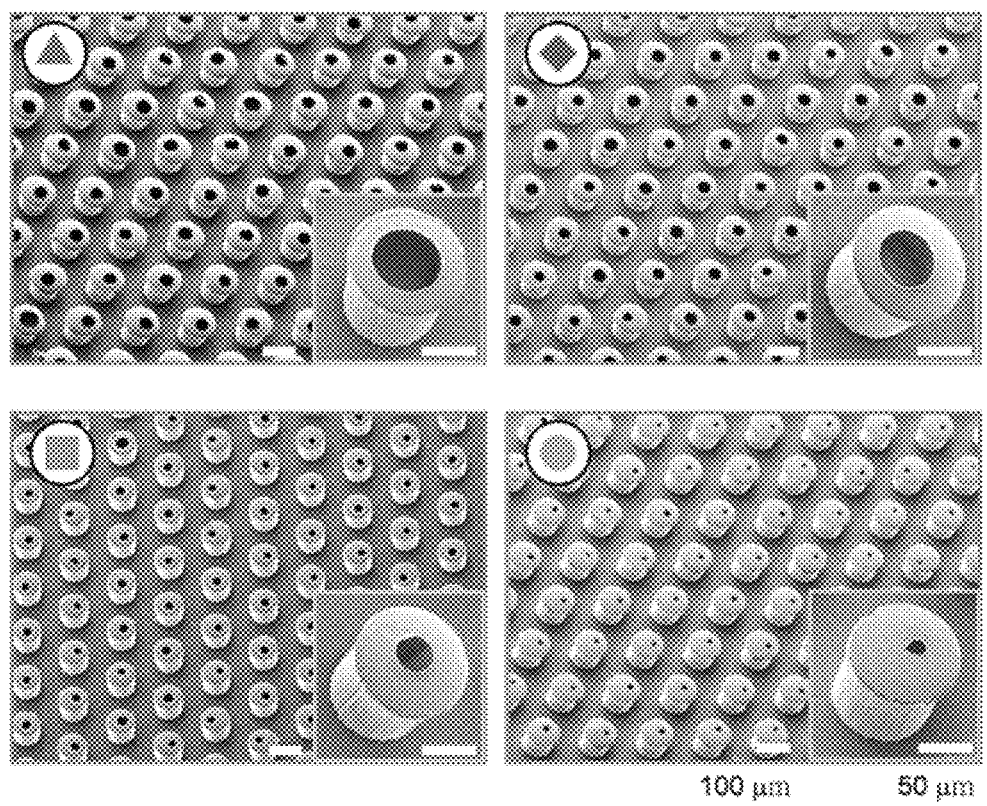
[FIG. 3A]
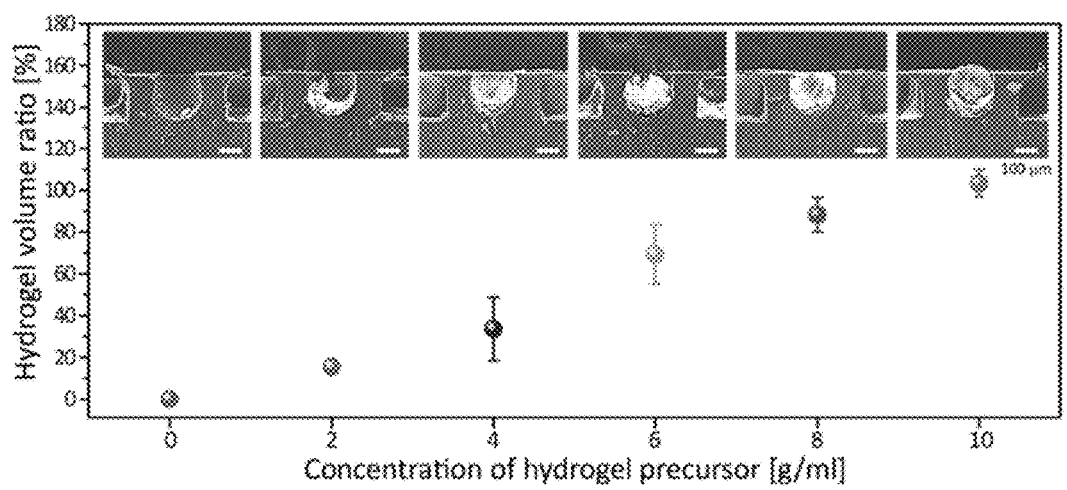

[FIG. 3B]
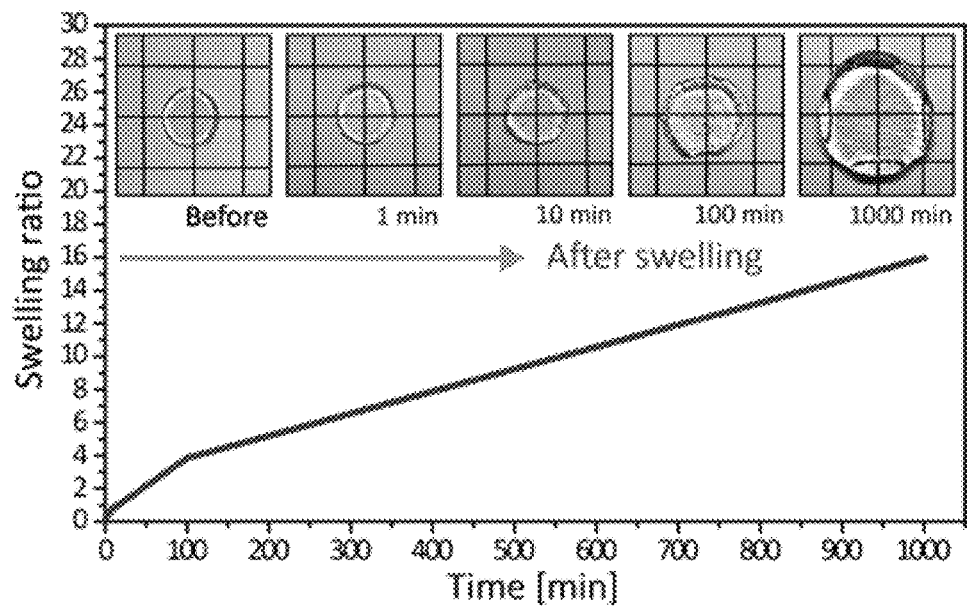
[FIG. 3C]
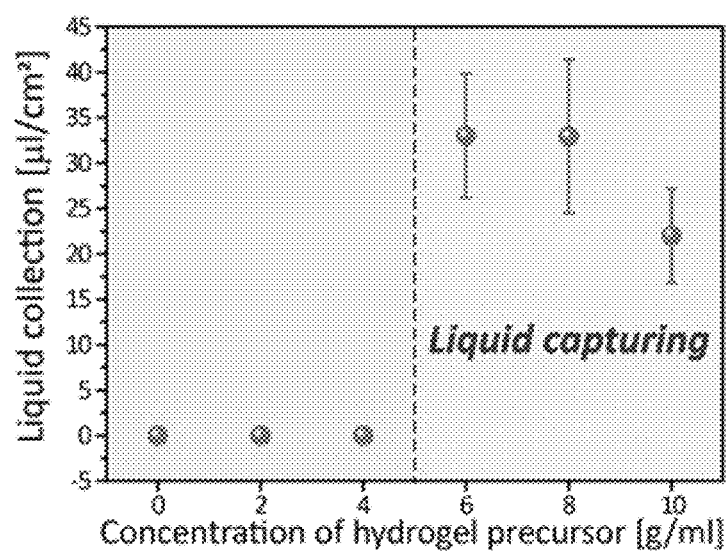

[FIG. 3D]
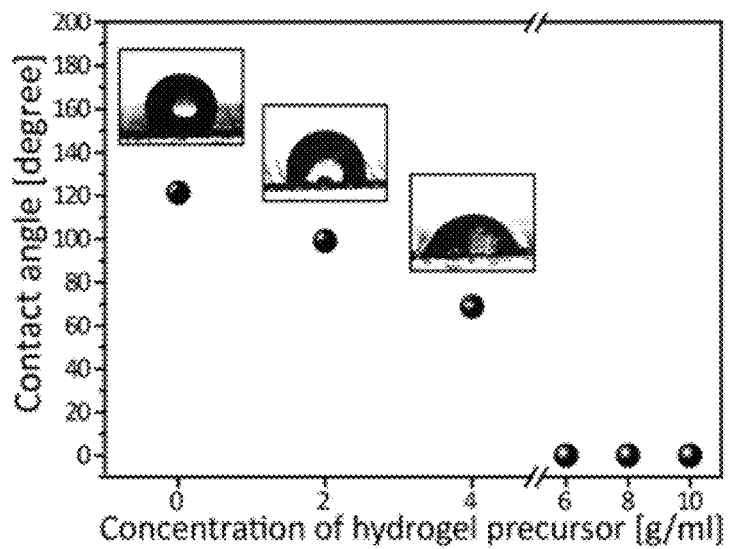
[FIG. 3E]
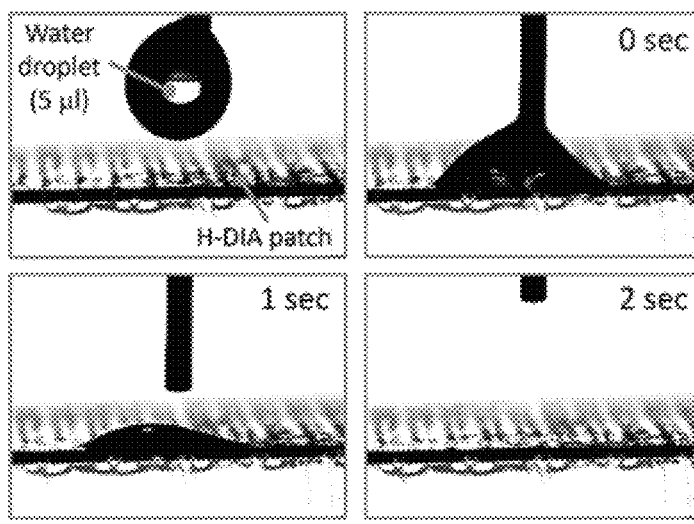

[FIG. 3F]
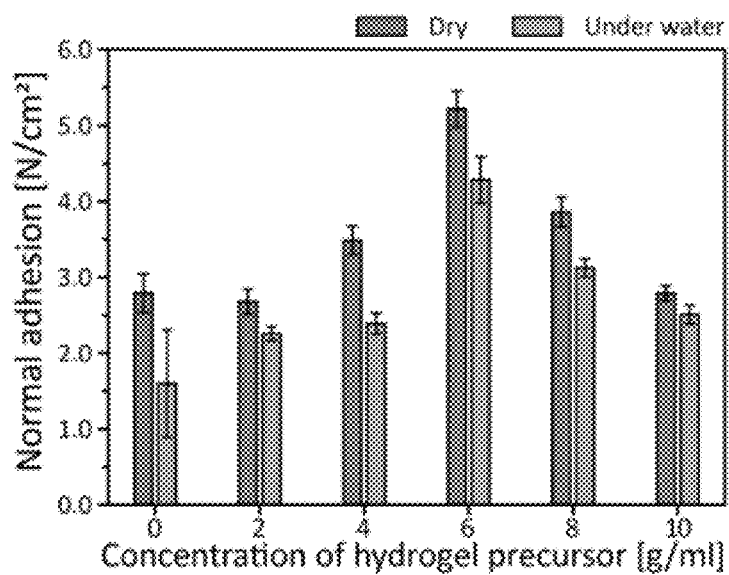
[FIG. 3G]
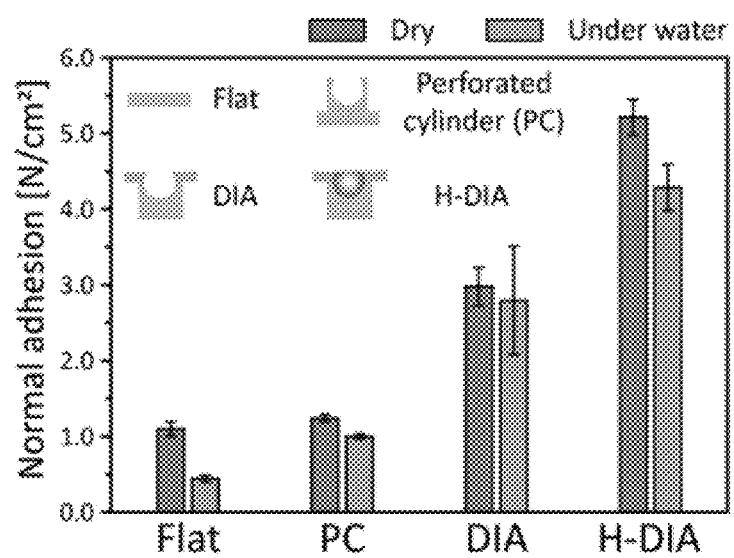

[FIG. 3H]
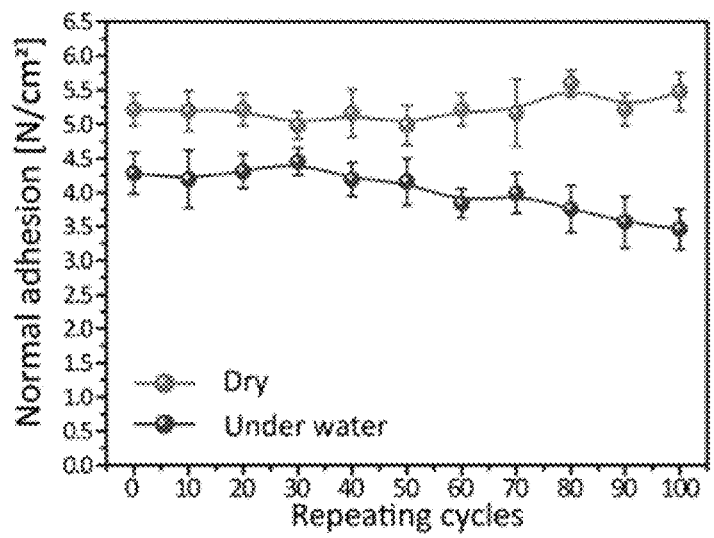
[FIG. 4A]
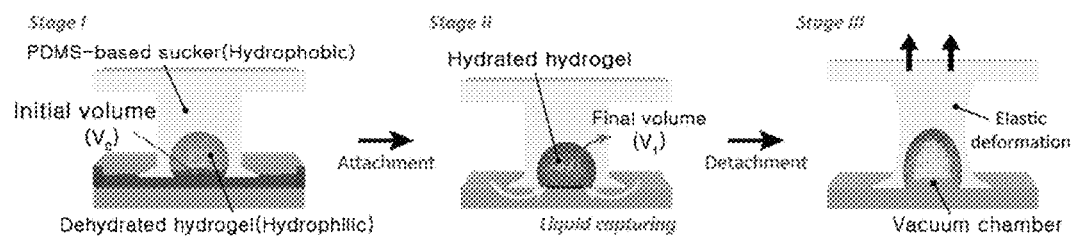
[FIG. 4B]
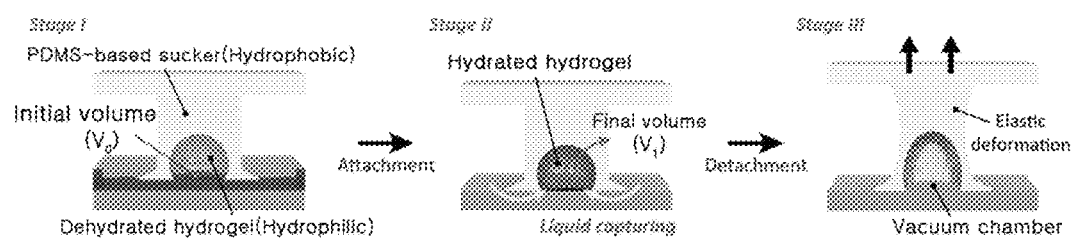

[FIG. 4C]
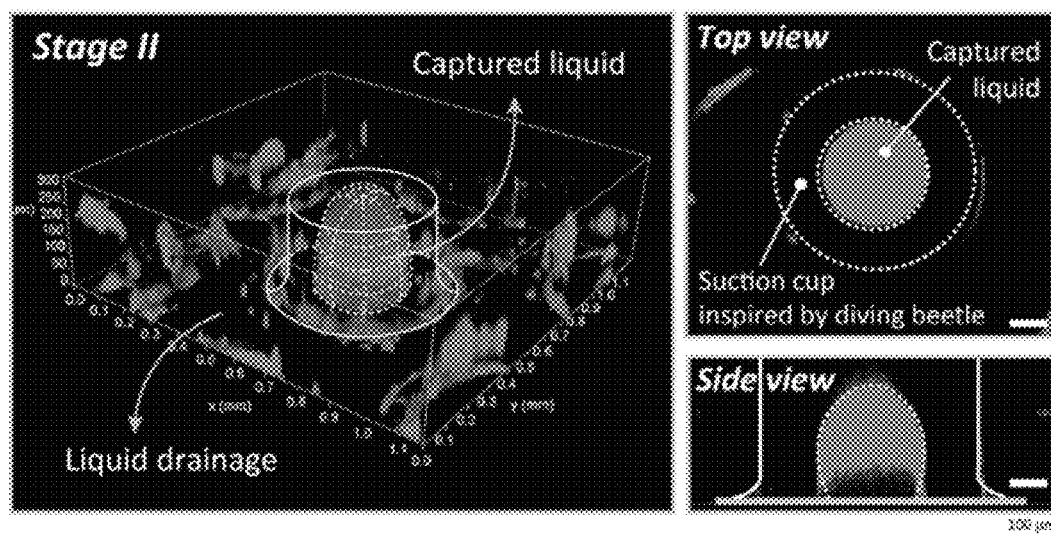
[FIG. 4D]
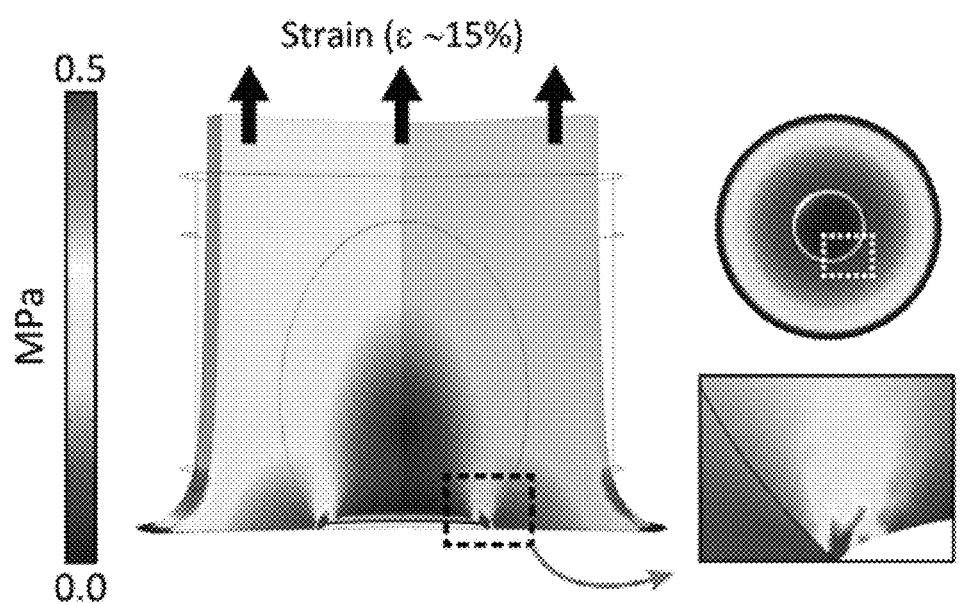

[FIG. 4E]
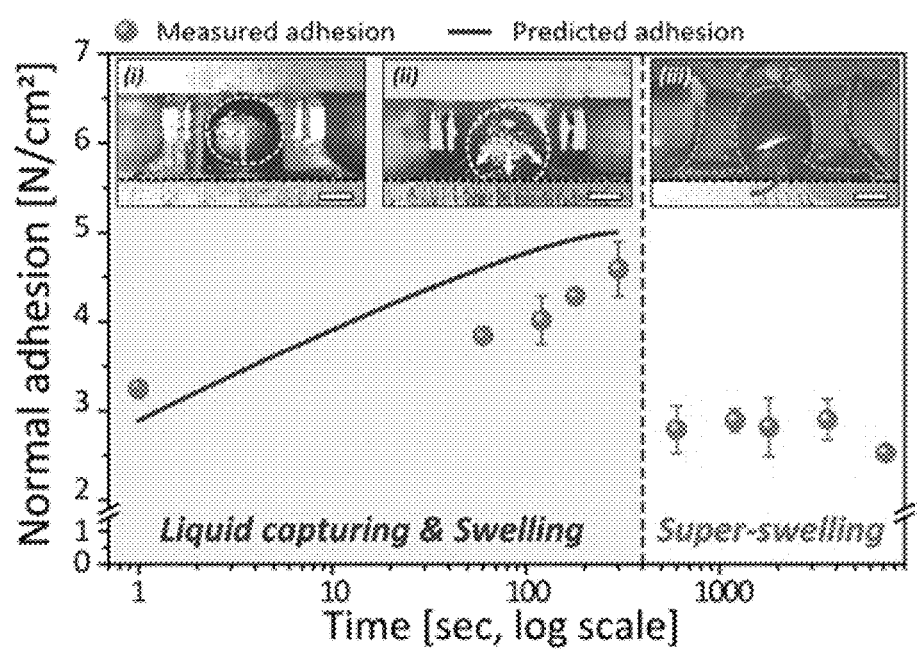

[FIG. 5A]
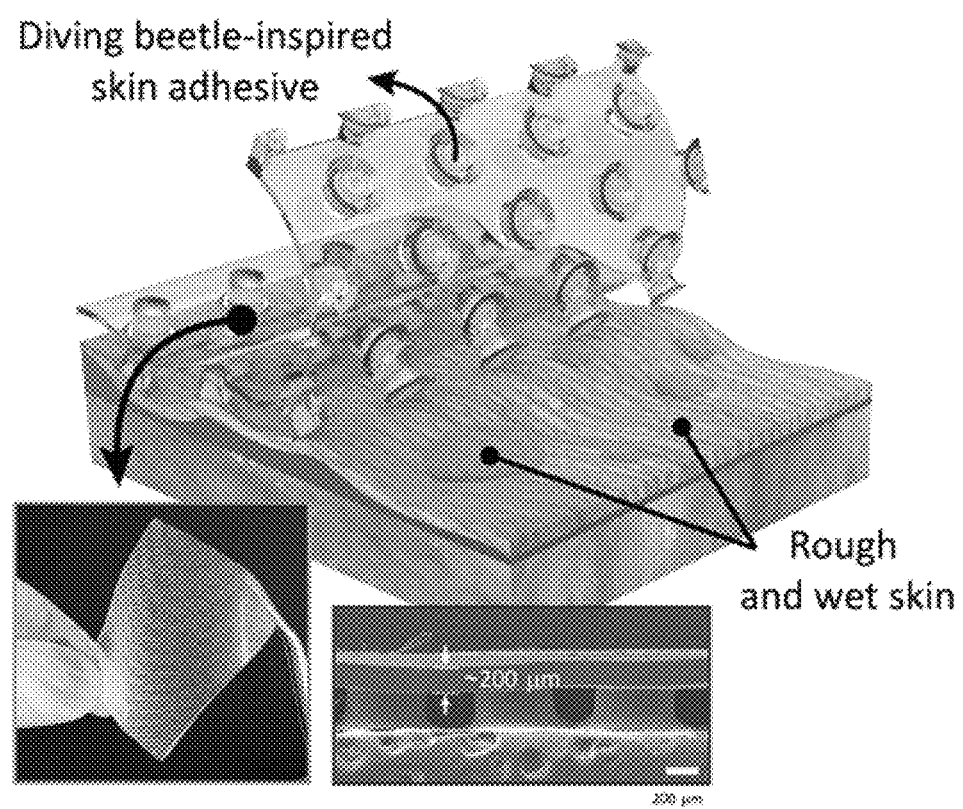

[FIG. 5B]
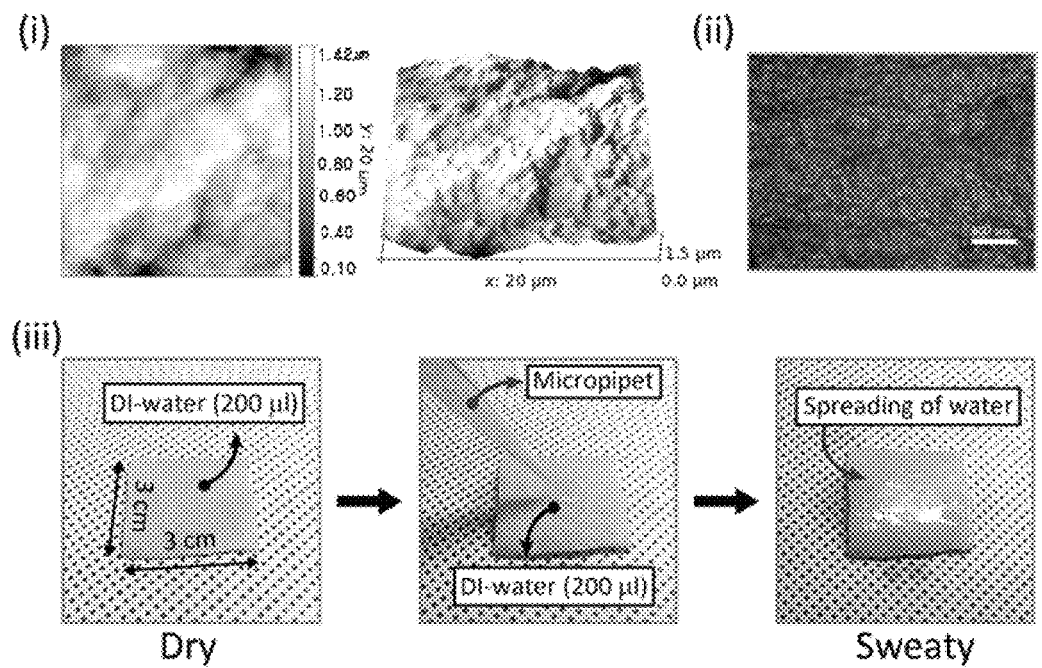
[FIG. 5C]
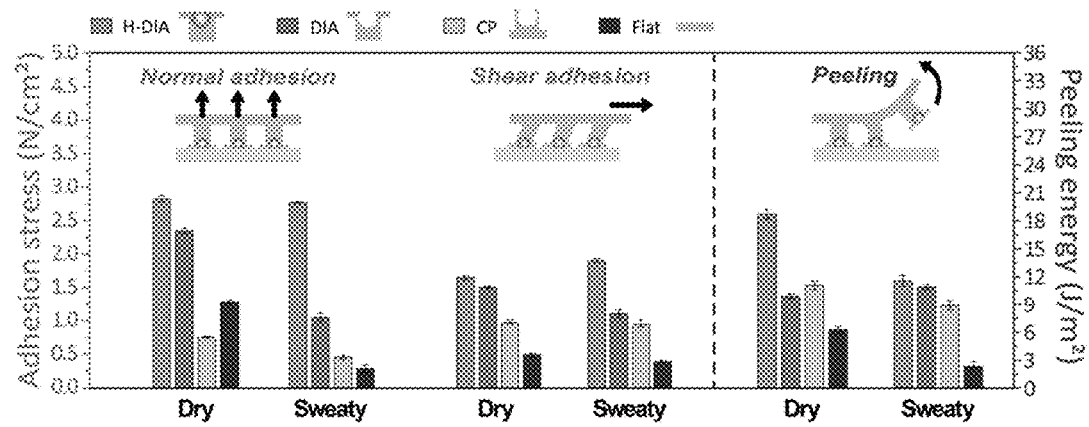

[FIG. 6A]
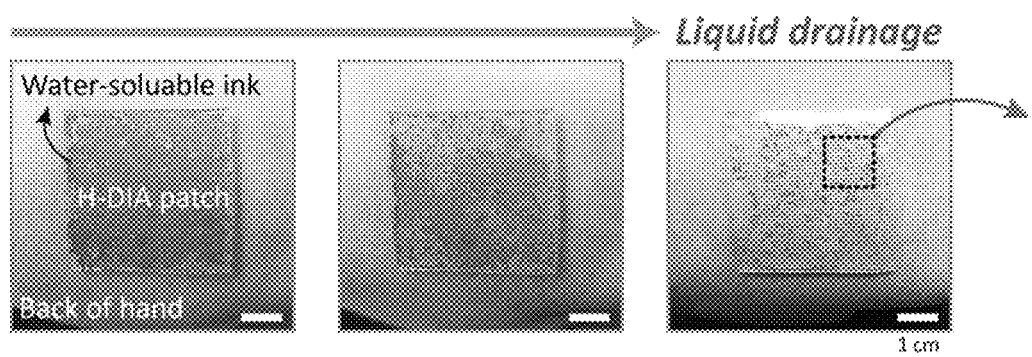
[FIG. 6B]
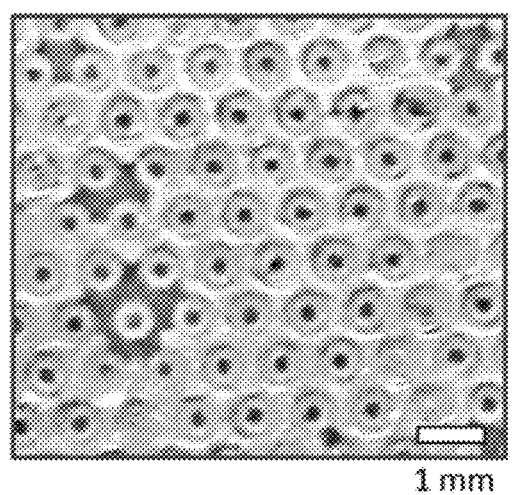

[FIG. 6C]
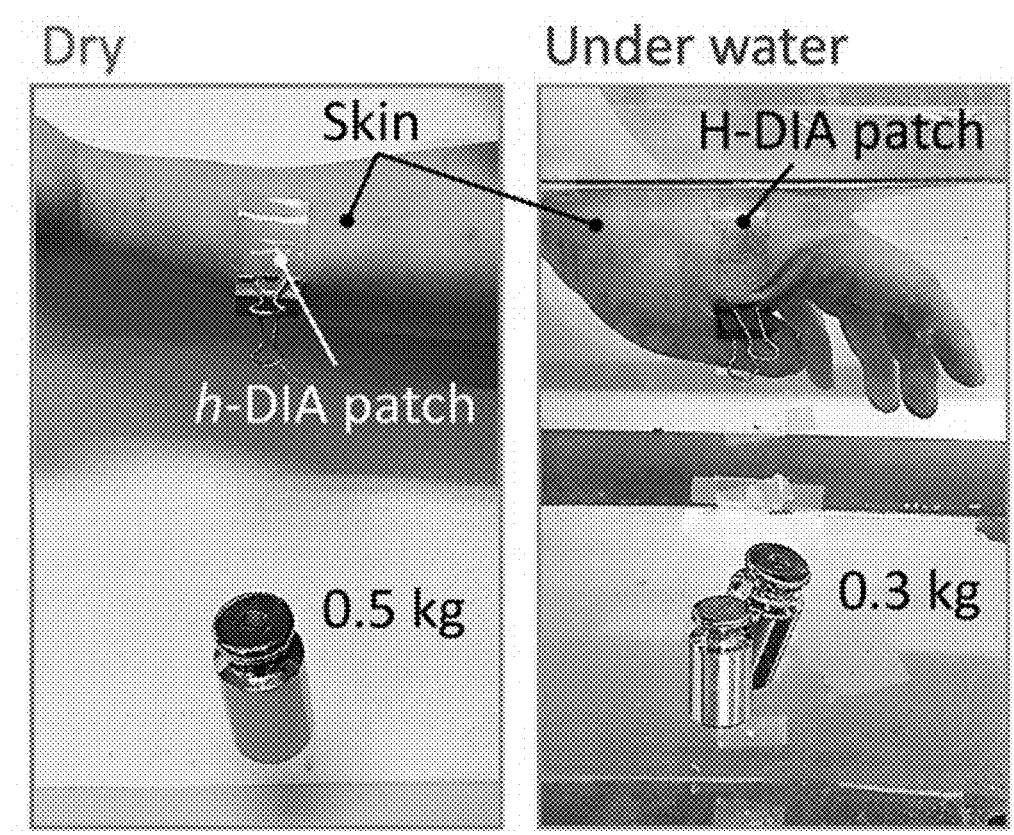

[FIG. 6D]
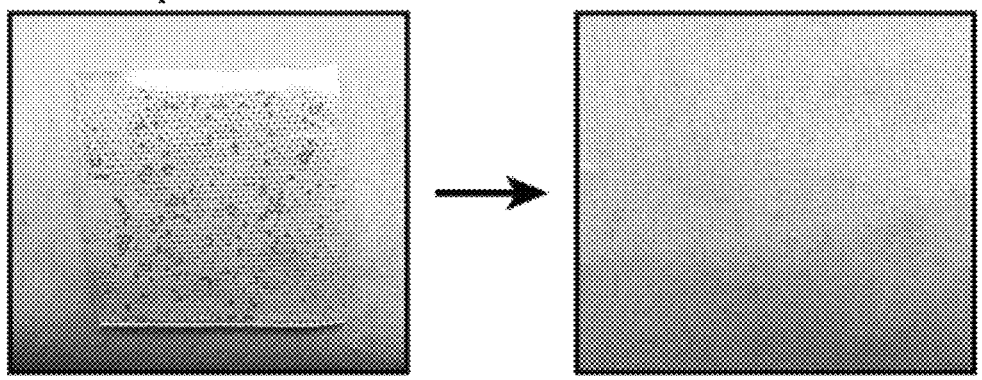
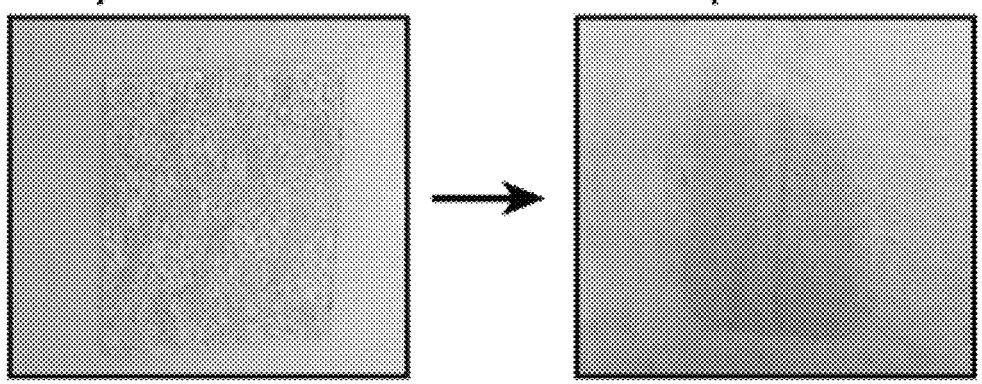

【FIG. 7】
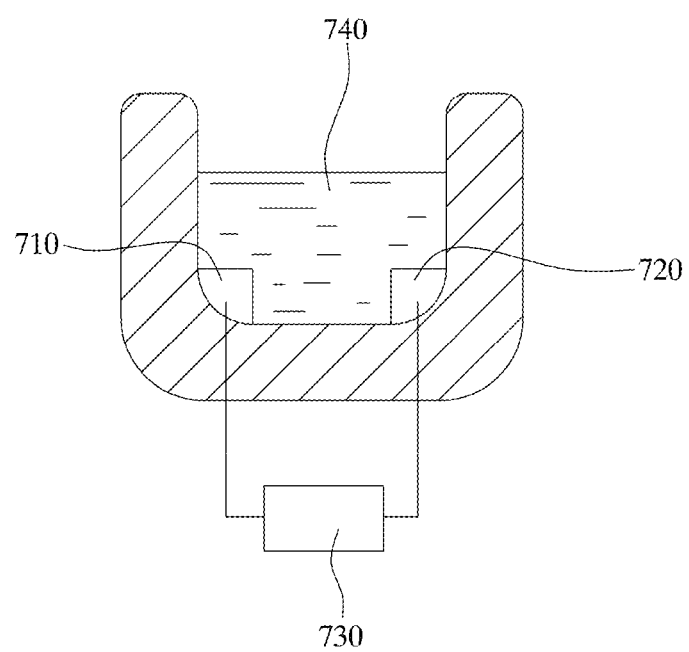

DRY ADHESIVE PATCH WITH MICRO-ABSORBENT HYBRID STRUCTURE CAPABLE OF CAPTURING AND CLEANLY-ADHERING BODY-FLUID AND MANUFACTURING METHOD THEREOF

CROSS-REFERENCE TO RELATED APPLICATION

This application claims a benefit under 35 U.S.C. § 119(a) of Korean Patent Application No. 10-2019-0017267 filed on Feb. 14, 2019, on the Korean Intellectual Property Office, the entire disclosure of which is incorporated herein by reference for all purposes.

BACKGROUND

1. Field

The present disclosure relates to a dry adhesive pad with a micro-adsorption structure that exhibits a high adhesive force even on a wet adhered surface or in an aquatic environment.

The present disclosure relates to an adhesive patch which mimics a micro-adsorption structure present on a forefoot of a male diving beetle that may be attached well thereto in an underwater environment, and in which a liquid capturing hydrogel material is inserted into an internal chamber defined in a micro adsorption plate, in which the patch may stably adhere to a wet surface of a body while effectively capturing a body fluid.

2. Description of Related Art

Currently, a market size of medical wearable devices for diagnosing and monitoring diseases in real time based on various analytical factors of a body, and drug delivery and treatment patches is growing rapidly. Accordingly, a dry adhesive based patch that stably adheres to a surface of a living body without side effects employs a conventional micro/nano manufacturing technology and thus becomes one of fields with high development potential. Thus, demand of the dry adhesive based patch increases and development of the dry adhesive based patch is required.

In particular, a field of a wearable device for capturing bio substances such as sweat, etc. from a skin of a living body and analyzing the substance is a very promising technical field. However, in the dry adhesive technology field, there is no technology for capturing the bio substance while stably adhering to the skin.

SUMMARY

This Summary is provided to introduce a selection of concepts in a simplified form that are further described below in the Detailed Description. This Summary is not intended to identify all key features or essential features of the claimed subject matter, nor is it intended to be used alone as an aid in determining the scope of the claimed subject matter.

A purpose in accordance with the present disclosure is to provide a dry adhesive patch that satisfies the demand of the technology development as above-described and to provide a body fluid capturing and analysis device using the dry adhesive patch.

Purposes in accordance with the present disclosure are not limited to the above-mentioned purpose. Other purposes and advantages in accordance with the present disclosure as not mentioned above may be understood from following descriptions and more clearly understood from embodiments in accordance with the present disclosure. Further, it will be readily appreciated that the purposes and advantages in accordance with the present disclosure may be realized by features and combinations thereof as disclosed in the claims.

In one aspect of the present disclosure, there is provided a dry adhesive patch comprising: a plurality of embossed pillars formed on a substrate; a hemi-spherical adsorbing cup defining a top portion of each pillar, wherein a hemi-spherical hole is defined in a top portion of the adsorbing cup and is exposed to an outside; and an annular extension extending radially from an outer perimeter of a distal end of each adsorbing cup.

In this connection, the substrate in accordance with the present disclosure means a base plate or the like used for the skin adhesive patch and may preferably be a flexible and breathable substrate. Any substrate used for the conventional skin patches may be used.

The hemi-spherical adsorbing cup may be embodied as a cap. Actually, the hemi-spherical adsorbing cup may be smaller than a complete hemi-spherical adsorbing cup.

The annular extension in accordance with the present disclosure may extend from the outer perimeter of the embossed pillar outwardly in a direction perpendicular to a length direction of the embossed pillar.

As used herein, the dry adhesion means bonding the patch to a target surface such as a skin surface not using a chemical adhesive but using structural characteristics of an adhesive surface of the patch. For example, the dry adhesion means adhesion using negative pressure related to van der Waals force or the adsorbing cup structure.

In accordance with the present disclosure, strong adhesion between the patch and the dry target surface or the patch and the wet target surface may be achieved due to the combination of the annular extension and the adsorbing cup.

In one implementation, a hydrogel is received in the hemi-spherical hole of the adsorbing cup. In one implementation, the hydrogel contains a hydrophilic functional group. In one implementation, the hydrogel includes at least one selected from a group consisting of polyacrylamide, polyaniline, polyethylene glycol, and alginate. In one implementation, the hydrogel has a porous chain network shape. In one implementation, the hydrogel occupies 70% or greater of a volume of the hole defined in the adsorbing cup.

In one implementation, a diameter of the hemi-spherical hole defined in the adsorbing cup is smaller than a diameter of the adsorbing cup.

In one implementation, the dry adhesive patch containing the hydrogel exhibits higher adhesive force in wet and dry environments than the dry adhesive patch free of the hydrogel exhibits.

In one implementation, the dry adhesive patch having the annular extension exhibits higher adhesive force in wet and dry environments than the dry adhesive patch free of the annular extension exhibits.

In another aspect of the present disclosure, there is provided a biological skin surface patch for capturing a body fluid, the patch including the dry adhesive patch ad defined above.

In one implementation, the biological skin surface patch further comprises: a first electrode outwardly extending from the hole of the adsorbing cup; a second electrode outwardly extending from the hole of the adsorbing cup, wherein the second electrode is spaced from the second electrode, wherein each of the first and second electrodes is in contact with the hydrogel; and an electrical signal measuring unit connected to the first and second electrodes to measure an electrical signal to analyze a body fluid captured in the hydrogel.

In one aspect of the present disclosure, there is provided a method for manufacturing a dry adhesive patch, the method comprising: providing a mold substrate having embossed engraved patterns defined therein; providing a film having a polymer precursor solution applied thereon; placing the film on the mold substrate such that air is trapped in the embossed engraved patterns; pressing a back face of the film to convert the trapped air to an air bubble; curing the polymer precursor solution; separating the cured polymer precursor from the mold substrate to form embossed pillars; and stamping a sticky polymer onto a top face of each of the embossed pillars to form an adsorbing cup having an annular extension extending radially from a distal end thereof.

In one implementation, the method further comprises filling a hydrogel into the adsorbing cup.

Effects in accordance with the present disclosure may be as follows but may not be limited thereto.

In accordance with the present disclosure, a new bio-friendly adhesive interface structure may be realized which mimics the micro sucker structure (adsorption plate) present on a forefoot of the diving beetle to secure air permeability and induce negative pressure in the water so that the interface structure may be strongly attached to a target surface in multiple directions. Thus, the present disclosure may realize a creative design and a manufacturing method for the adhesive patch optimized for dry and wet environments.

In accordance with the present disclosure, the hydrogel-based material capable of capturing and maintaining the moisture therein may be inserted into the chamber inside the above described micro-adsorption structure. Thus, the present disclosure may provide a novel interface system that may capture and hold sweat, blood and dust on the surface of the living body to improve the performance of the body fluid capturing and analysis. Further, the system may be expected to amplify the adhesive force with the biological surface in a humid environment.

In accordance with the present disclosure, applications incorporating the adhesive system as described above may be developed. Specifically, the patch may be combined with various existing electronic materials and devices to achieve a body fluid analysis sensor patch that may monitor various health information as indicated by the captured body fluid. Further, an active ingredient, drug delivery system, stem cells and the like may be received in the micro chamber and then the patch may be closely adhered to the target surface of the living body to realize a medical patch system to induce a high-efficiency therapeutic effect.

In addition to the effects as described above, specific effects in accordance with the present disclosure will be described together with the detailed description for carrying out the disclosure.

BRIEF DESCRIPTION OF DRAWINGS

FIGS. 1A-1F illustrate a dry adhesive pad in accordance with the present disclosure.

FIGS. 2A-2C illustrate a method for manufacturing the dry adhesive pad in accordance with the present disclosure.

FIGS. 3A-3H illustrate an effect in accordance with the present disclosure.

FIGS. 4A-4E illustrate an adhesive mechanism in accordance with the present disclosure.

FIGS. 5A-5C illustrate an actual fabricated dry adhesive pad and an effect thereof in accordance with the present disclosure.

FIGS. 6A-6D illustrate an effect of an actual fabricated patch in accordance with the present disclosure.

FIG. 7 illustrates a dry adhesive pad in accordance with the present disclosure comprising electrodes.

DETAILED DESCRIPTIONS

For simplicity and clarity of illustration, elements in the figures are not necessarily drawn to scale. The same reference numbers in different figures denote the same or similar elements, and as such perform similar functionality. Further, descriptions and details of well-known steps and elements are omitted for simplicity of the description. Furthermore, in the following detailed description of the present disclosure, numerous specific details are set forth in order to provide a thorough understanding of the present disclosure. However, it will be understood that the present disclosure may be practiced without these specific details. In other instances, well-known methods, procedures, components, and circuits have not been described in detail so as not to unnecessarily obscure aspects of the present disclosure.

Examples of various embodiments are illustrated and described further below. It will be understood that the description herein is not intended to limit the claims to the specific embodiments described. On the contrary, it is intended to cover alternatives, modifications, and equivalents as may be included within the spirit and scope of the present disclosure as defined by the appended claims.

The terminology used herein is for the purpose of describing particular embodiments only and is not intended to limit the present disclosure. As used herein, the singular forms "a" and "an" are intended to include the plural forms as well, unless the context clearly indicates otherwise. It will be further understood that the terms "comprises", "comprising", "includes", and "including" when used in this specification, specify the presence of the stated features, integers, operations, elements, and/or components, but do not preclude the presence or addition of one or more other features, integers, operations, elements, components, and/or portions thereof. As used herein, the term "and/or" includes any and all combinations of one or more of the associated listed items. Expression such as "at least one of" when preceding a list of elements may modify the entire list of elements and may not modify the individual elements of the list.

It will be understood that, although the terms "first", "second", "third", and so on may be used herein to describe various elements, components, regions, layers and/or sections, these elements, components, regions, layers and/or sections should not be limited by these terms. These terms are used to distinguish one element, component, region, layer or section from another element, component, region, layer or section. Thus, a first element, component, region, layer or section described below could be termed a second element, component, region, layer or section, without departing from the spirit and scope of the present disclosure.

In addition, it will also be understood that when a first element or layer is referred to as being present "on" or "beneath" a second element or layer, the first element may be disposed directly on or beneath the second element or may be disposed indirectly on or beneath the second element with a third element or layer being disposed between the first and second elements or layers.

It will be understood that when an element or layer is referred to as being "connected to", or "coupled to" another element or layer, it may be directly on, connected to, or coupled to the other element or layer, or one or more intervening elements or layers may be present. In addition, it will also be understood that when an element or layer is referred to as being "between" two elements or layers, it may be the only element or layer between the two elements or layers, or one or more intervening elements or layers may also be present.

Further, as used herein, when a layer, film, region, plate, or the like is disposed "on" or "on a top" of another layer, film, region, plate, or the like, the former may directly contact the latter or still another layer, film, region, plate, or the like may be disposed between the former and the latter. As used herein, when a layer, film, region, plate, or the like is directly disposed "on" or "on a top" of another layer, film, region, plate, or the like, the former directly contacts the latter and still another layer, film, region, plate, or the like is not disposed between the former and the latter. Further, as used herein, when a layer, film, region, plate, or the like is disposed "below" or "under" another layer, film, region, plate, or the like, the former may directly contact the latter or still another layer, film, region, plate, or the like may be disposed between the former and the latter. As used herein, when a layer, film, region, plate, or the like is directly disposed "below" or "under" another layer, film, region, plate, or the like, the former directly contacts the latter and still another layer, film, region, plate, or the like is not disposed between the former and the latter.

Unless otherwise defined, all terms including technical and scientific terms used herein have the same meaning as commonly understood by one of ordinary skill in the art to which this inventive concept belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

As used herein, the term "substantially," "about," and similar terms are used as terms of approximation and not as terms of degree, and are intended to account for the inherent deviations in measured or calculated values that would be recognized by those of ordinary skill in the art. Further, the use of "may" when describing embodiments of the present disclosure refers to "one or more embodiments of the present disclosure."

FIGS. 1A-1G illustrate an appearance of a dry adhesive pad in accordance with the present disclosure. FIG. 1A shows a micro adsorbing cup present on a forefoot of a male diving beetle. The micro adsorbing cup has a mushroom-like extended distal end that expands a contact area, and a spherical empty space (suction chamber) that may induce a negative pressure. This structure allows close and effective adhesion to a rough surface of a female diving beetle underwater.

In accordance with the present disclosure, as shown in FIG. 1B, a hydrogel-embedded structure mimics the structural characteristics of the diving beetle and is capable of capturing liquid and has a high adhesive force in multiple directions. As used herein, the hydrogel-embedded structure may be referred to as a hydrogel-embedded diving beetle-inspired architecture (H-DIA).

In this connection, as shown in FIG. 1C, the hydrogel inserted into the microstructure of the present patch may be made of polyacrylamide (PAAm) and has polymer chains intertwined with each other and having hydrophilic functional groups. Referring to FIG. 1D and FIG. 1E, an optical/electron microscope image shows that micro adsorbing cup structures are uniformly arranged. As shown in FIG. 1F, the hydrogel inserted into the adsorbing cup in accordance with the present disclosure has a porous chain network that may efficiently capture liquid.

FIGS. 2A-2C illustrate a method for manufacturing the dry adhesive pad in accordance with the present disclosure. The dry adhesive pad is manufactured by mimicking a circular adsorbing cup structure on the forefoot of the male diving beetle and using a solution process-based molding method.

As shown in FIGS. 2A-2C, a polymer-based perforated cylinder may be fabricated by trapping air bubbles in patterns of a master mold (air-trapping technique) ((i) in FIG. 2A; diameter 100 μm, height 100 μm, distance between patterns 100 μm). In this connection, the polymer as used is a polyurethane acrylate (PUA)-based UV curable polymer and is UV cured on a PET film whose surface is treated to be chemically bonded to the PUA. Specifically, the PET film is placed on a PUA precursor solution and then various pressure is applied thereto using a custom-made extruder to adjust a volume of the air bubble inside the pattern (reference is made to (ii) in FIG. 2A).

Next, the PUA precursor solution is exposed to UV for 30 seconds to cure the PUA precursor to produce the perforated cylinder (hereafter, referred to as "PC").

Next, for the structure (DIA) that enables adhesion and close contact with a surface, a PDMS-based sticky and soft PDMS (s-PDMS) is partially applied on a distal end of the PC structure and is cured. Thus, a structure in which the distal end of the cylinder is widened is produced (reference is made to (iii) in FIG. 2A). In this connection, s-PDMS may be synthesized by a simple process that mixes a very small amount of ethoxylated polyethylenimine (PEIE) with a solution precursor of PDMS and cure the mixture.

As shown in FIG. 2B, a volume of a spherical chamber inside the DIA structure may be controlled based on a pressure applied thereto before the curing of the polymer. As a result, when the smallest pressure of 10 kPa is applied thereto, a volume of the trapped air bubble is found to be the largest. This means that an amount of the hydrogel inserted into the chamber for sweat capturing increases.

In this connection, a simple theoretical model is designed to predict the volume of the internal chamber based on variables such as adhesive material properties, structural factors, and applied pressure. This model is derived based on a force balance of an air pressure of the air bubble due to a surface capillary force, an external pressure, and Boyle's law formed between three phases of the polymer precursor (liquid), air bubble (vapor), and silicon master mold (solid) within the micro-sized micro-pattern. Therefore, a theoretical model of a radius of the air bubble (the internal chamber of the PC) trapped inside the pattern based on the external pressure is expressed as a following equation:

$$R(P_c) = \left[\frac{P_0 r^3 H}{(2\gamma\cos\theta + rP_c)\left(\cos\theta - \cos^3\theta + \frac{2}{3}\right)\pi}\right]^{1/3}$$

The model predicts the volume of the internal chamber of the PC produced at an external pressure of 10 to 190 kPa. The theoretical prediction has been confirmed to have a similar trend with an experimental result (FIG. 2A). FIG. 2C is an electron microscope image of a micro PC structure with an internal chamber whose size is varied according to the external pressure.

Next, the polyacrylamide (PAAm)-based hydrogel is inserted into the internal chamber of the fabricated structure (DIA) in order to maximize sweat capturing ability. In this connection, a DIA structure of 500 μm diameter and 300 μm height is selected to maximize a capturing amount of sweat. Further, the volume of the hydrogel inserted into the chamber is controlled by adjusting a concentration of AAm monomer in a range of 0 to 10 g/ml (FIG. 3A). An inset of FIG. 3A shows electron microscope images of cross-sections of the hydrogels filled in the chamber based on various precursor concentrations. This result indicates that the volume of the hydrogel inserted into the DIA may be controlled based on the concentration of the hydrogel aqueous solution. Further, in order to analyze a moisture absorbing ability of the PAAm-based hydrogel, we observe swelling behavior due to moisture absorption over time (FIG. 3B). According to the previously studied theories, the swelling phenomenon of hydrogel is defined as a swelling ratio (SwR) as follows:

$$SwR = \frac{m_s - m_i}{m_i}$$

The SwR of the PAAm hydrogel increases by about 1,600% for 1,000 min. Therefore, it is expected that the hydrogel with this characteristic as inserted into the chamber may absorb the moisture efficiently.

To analyze the moisture capturing ability of the hydrogel-embedded diving beetle-inspired adhesive structure (H-DIA), we measure a volume of distilled water absorbed into the structure (FIG. 3C). As a result, it is confirmed that the H-DIA structure which occupies 70% of the internal chamber captures 30 μl of distilled water per 1 cm². Such performance characteristics may be considered as the ability to fully capturing an average amount of sweat (about 12 to 120 μl/hour·cm²) that one person releases on a daily basis.

On the contrary, the H-DIA structure which occupies a volume smaller than 70% of the internal chamber is unable to capture water droplets. This is because an amount of the filled hydrogel is too small to react with external water molecules, such that the hydrogel may not interact with the water droplets, and the hydrophobic PDMS-based adsorbing cup structure repels the water molecules.

FIG. 3D shows the contact angle between the surface and H-DIAs with varying amounts of the filled hydrogel. Interestingly, when the H-DIA structure occupies a volume larger than or equal to 70% of the internal chamber, the contact angle could not be determined because the water droplet is immediately absorbed into the hydrogel (absorption rate: 2.5 μl/sec·cm² (see FIG. 3E.) However, the PAAm film without the H-DIA structure exhibits no immediate water absorption despite the PAAm film is made of a super-hydrophilic material. Thus, when the micro sized adsorbing cup structure and the super-hydrophilic hydrogel material are combined with each other to complement each other, the above mentioned effect may be achieved.

Next, in order to analyze the adhesive force of the H-DIAs having various amounts of the filled hydrogel, a vertical adhesive force thereof with a silicon substrate is measured in a dry/wet environment (FIG. 3F). The adhesion test is executed using customized equipment. A preload of 1 N/cm² is applied to the substrate at room temperature (the preload refers to a force applied to the substrate before measuring the adhesive force). Further, the structural properties of the adhesive of various structures (H-DIA, DIA, PC, and flat samples) are compared with each other (FIG. 3G). As a result, H-DIA using 6 g/ml hydrogel precursor concentration showed the highest adhesive force in both dry and wet environments. This is due to the surface characteristics of s-PDMS including close contact with the surface and increasing the surface energy, the diving beetle mimicked structure that may induce the adsorption, and the material properties of the hydrogel that may absorb and drain excess moisture. FIG. 3H shows that the present biomimetic adhesive has good repeatability of the adhesive force in dry/humid environments (about 100 repetitions).

A specific adhesive mechanism of the patch in accordance with the present disclosure is as follows. As shown in FIG. 4A, the H-DIA first contacts the substrate in the moisture environment (Stage I). when a small preload is applied thereto, the surface of the hydrophobic PDMS-based adsorbing cup repels water molecules into the chamber where the hydrogel is inserted. In this connection, the hydrogel is hydrophilic and dry, and thus may easily absorb the water molecules, thus leading to change in the volume inside the chamber (Stage II in (a) in FIG. 4). Once the hydrogel has absorbed the maximum moisture it may contain, liquid capturing is completed. In this connection, the hydrogel swells to the maximum degree and, thus, the volume inside the chamber reaches a minimum value. Thereafter, in a desorption process, the elastic polymer based H-DIA undergoes structural deformation. In this connection, in the internal chamber, a vacuum-like environment instantaneously occurs. This may lead to an adsorption effect by which the structure may strongly adhere to the surface (Stage III).

The present inventors observe the capturing of moisture by the hydrogel using confocal fluorescence microscopy. Specifically, after mixing a fluorescent substance with water, the behavior of water molecules is checked when the H-DIA contacts the wet surface. FIG. 4B shows a situation where a dry hydrogel-embedded H-DIA is in contact with the wet surface. After the adhesion process with the surface is completed, the mixed liquid between the fluorescent substance and water is sucked into the adsorbing cup (FIG. 4C). Finite element method (FEM) simulation shows that a stress is concentrated inwardly of a contact interface between the micro chamber and the contacted surface when the adhesive patch is removed (FIG. 4D). This contributes to forming a chamber having a state similar to a vacuum state. To explain the suction effect-based adhesion mechanism via liquid capturing by the hydrogel, a simple mathematical model is presented. Specifically, a difference between internal and external pressures may be induced based on the change in the pressure of the internal chamber as generated when the inserted hydrogel sucks the moisture. Further, the pressure in the internal chamber is due to the volume expansion effect of the hydrogel. Thus, a following equation may be derived based on a volume expansion rate of the hydrogel on the wet surface over time and the structural/material related variables of the adsorbing cup:

$$\sigma_S = P_0 \pi r^2 n \left[ \frac{V_0 m_0}{V_C m_0 - V_{h,0} m_{max} + V_{h,0} m_0 A_S \exp\left(\frac{-t}{\tau_S}\right)} - 1 \right]$$

The model based on the liquid capturing and associated hydrogel expansion rate theoretically predicts an increase in the adhesive force on wet surfaces over time and exhibits a trend similar to experimental result values (FIG. 4E). On the other hand, the adhesive patches of different structures show that the adhesive forces thereof remain unchanged over time.

However, after a certain time duration, the adsorption effect between each adhesive patch and the surface disappears due to overexpansion of the hydrogel and thus the adhesive force thereof decreases.

The diving beetle mimetic patch in accordance with the present disclosure is potentially applicable to human skin (FIG. 5A). In order to evenly contact the patch with a curved skin surface, the adhesive patch has a thin film form (about 200 μm thickness; electron microscope image of FIG. 5A). Then, adhesion performance is measured on the surface of a swine skin most similar to a surface of human skin. The adhesive force test is performed on the swine skin of 3×3 $cm^2$, and on a dry swine skin surface or a wet swine skin surface on which micro water droplets such as sweats are present.

In particular, as shown in an atomic force microscopy (AFM) data of (i) of FIG. 5B, the three-dimensional shape of the swine skin surface has high roughness, wrinkles, and irregular surface morphology to lower the adhesion performance ((ii) in FIG. 5B). Further, 200 μl of distilled water is applied on dry swine skin to create a sweaty surface condition ((iii) in FIG. 5B). Compared to adhesive patches having different microstructures, the H-DIA based skin adhesive patch may exhibit the highest adhesion performance with the dry/wet swine skins in a normal direction (about 2.8 $N/cm^2$ on the dry surfaces; about 2.8 $N/cm^2$ on the wet surfaces) and in a shear direction (about 1.6 $N/cm^2$ on the dry surfaces; about 1.8 $N/cm^2$ on the wet surface) (FIG. 5C). This is caused by the combination of the high adhesive force between the skin and the s-PDMS tip and the moisture drainage effect of the hydrogel. This property also affects a peeling strength from the skin surface, resulting in high peeling energy (about 19 $J/m^2$ on dry surfaces; about 12 $J/m^2$ in wet environments).

The present disclosure demonstrates that the H-DIA skin patch is firmly and cleanly adhered to the skin. As shown in FIG. 6A, when the H-DIA patch is applied on the skin, a mixture of water and water-soluble ink is drained from the surface of the skin into the chamber of the H-DIA (FIG. 6B). Photographic data in FIG. 6C shows that the H-DIA may hold 0.5 kg of a weight on the dry skin and may hold 0.3 kg of a weight on the wet skin. Further, when the adhesive patch is applied to the back of the subject's hand and, then, after 6 hours, is removed therefrom, there are no residues on the skin surface or no skin damage such as redness or peeling of the skin surface (FIG. 6D). This property has the advantage of overcoming various side effects (chemical residue, peeling of skin, rash, etc.) of the conventional acrylic based chemical adhesives (FIG. 6D).

The present disclosure provides an adhesive patch that mimics the adsorbing cup on the forefoot of the diving beetle and provides a liquid capturing surface that induces a clean and highly adhesive force on the sweaty skin surface. The present disclosure examines the structural properties of the H-DIA and the properties of the hydrogels embedded therein. In particular, the adhesive force and liquid capturing performance in wet environments are analyzed. The high adhesive force of the biomimetic adhesive patch is due to a combination of the adsorption effect occurring in the chamber of the diving beetle mimicked adsorbing cup and the structural properties of the mushroom-shaped widened tip contacting the coarse surface. Further, inserting the hydrogel inside the three-dimensional structure may allow maximizing the moisture capturing ability and draining the excess moisture to secure the high adhesive force. In this way, a liquid capturing interface for the precise analysis of sweat is proposed in accordance with the present disclosure. Furthermore, the biomimetic structure could be combined with various biosensors to provide a new platform that may increase accuracy of efficient and non-invasive sweat analysis and accuracy of analysis of various bio signals.

The present disclosure illustrates the structures of electrodes in the patch of the present invention in FIG. 7. The biological skin surface patch further comprises a first electrode 710 outwardly extending from the hole of the adsorbing cup; a second electrode 720 outwardly extending from the hole of the adsorbing cup, wherein the second electrode is spaced from the second electrode, wherein each of the first and second electrodes is in contact with the hydrogel 740; and an electrical signal measuring unit 730 connected to the first and second electrodes to measure an electrical signal to analyze a body fluid captured in the hydrogel.

Manufacturing Method (1) Fabrication of DIA Adhesive Patch

Photolithography and reactive ion etching processes are used to fabricate silicon molds with micro-cup patterns of various sizes (diameter: 100 μm, 500 μm; width-depth ratio: 1). The molds are treated with a fluorineated-self-assembled monolayer solution (tridecafluoro-1,1,2,2-tetrahydrooctyl)-trichlorosilane (FOTCS) as diluted in 0.03 M anhydrous heptone under argon gas. The prepared mold is fixed on a top of a customized press machine using cyanoacrylate paste. Liquid precursor (s-PUA) is then applied onto a PET (polyethylene terephthalate film (thickness 50 μm for a backbone) (Supplementary FIG. 1A). To precisely control the volume of the trapped air bubble, the polymer precursor and the mold having the cup structural patterns are compressed at a pressure from 10 kPa to 190 kPa ((ii) in FIG. 2A). Subsequently, ultraviolet rays placed in the press machine are irradiated to the polymer precursor for 2 minutes. Peeling off the cured s-PUA/PET film yields the perforated cylinder (PC). In order to completely cure the mold (replica) formed using the PUA, ultraviolet rays are further irradiated thereto for a few hours. The PDMS is used to fabricate a dense PC structure array using a simple replica molding process.

Next, in order to produce a mushroom-shaped cylinder (DIA) having a micro hole defined therein, a liquid precursor of s-PDMS (composed of PEIE 40 μl and PDMS 10 g) is thinly coated on a glass substrate at 1200 rpm for 60 seconds. A patch having the PC structure is transferred onto the glass substrate on which the thin s-PDMS layer is present. Then, only a top of the cylinder is selectively stamped for 10 seconds without external pressure being applied thereto. The stamped adhesive patch is transferred onto a clean glass substrate while the PC structure faces downward and is cured at 90 degrees C. for 2 hours.

(2) Preparation of PAAM Hydrogel

While controlling the amount of the precursor, hydrogels of various concentrations thereof (0.2 g/ml, 0.4 g/ml, 0.6 g/ml, 0.8 g/ml, and 1 g/ml) are prepared. The precursor is composed of AAm (acrylamide), KPS (potassium persulfate) and water. In order to produce a pre-gel solution, the components of the precursor are mixed in a beaker and are stirred for 1 hour.

(3) Preparation of H-DIA Patch Containing Hydrogel

In order to put the pre-gel solution into the DIA micro holes, the prepared patch is first subjected to $O^2$ plasma treatment for 1 minute. Then, the patch is disposed on a Teflon coated substrate and then the pre-gel solution is input into the micro hole chamber. Optionally, a blotting paper is used to remove a remaining solution between micro pillars to fill the pre-gel solution into the holes. Finally, the sample is cured at 80 degrees C. for 2 hours.

(4) Adhesion Test

Normal and shear adhesion tests are executed on silicon wafers and swine skin (area: about 3×3 cm$^2$) at room temperature in dry (relative humidity: about 50%) and humid environments using a custom-made tester.

Dead swine skin is purchased from a local slaughterhouse and frozen and stored in a known manner [ref; Nature]. The swine skin is used to perform the skin adhesion tests because the swine skin has morphological characteristics similar to that of human skin. We cut the dead swine skin (area: about 3×3 cm$^2$), and immerse the same in distilled water for 2 hours. Then, we use a blotting paper to remove the distilled water from the surface of swine skin. To create a moist skin condition, 20 μl of water is applied on the swine skin with an area of 3×3 cm$^2$. This skin piece is used as the substrate. Then, the patch attached to a jig is placed adjacent to the substrate such that the patch does not touch the substrate. A preload (1.0 N/cm$^2$) is applied to the adhesive patch for 5 seconds and then the patch is removed from the substrate for measurement.

For a peeling adhesion test, the adhesive sample attached to the jig is evenly applied on the swine skin as the substrate at a specific peeling angle. The substrate jig moves up while the sample jig moves to a right at a constant speed (1 mm/sec) to maintain the peeling angle while measuring the peeling adhesive force.

The embodiments of the present disclosure as disclosed in the present specification and drawings are merely presented by way of example for clarity of understanding and is not intended to limit the scope of the present disclosure thereto. It is apparent to those skilled in the art that other modifications based on the technical spirit of the present disclosure may be implemented in addition to the embodiments disclosed herein.

What is claimed is:

1. A dry adhesive patch comprising:
    a plurality of embossed pillars formed on a substrate;
    a hemi-spherical adsorbing cup defining a top portion of each pillar, wherein a hemi-spherical hole is defined in a top portion of the adsorbing cup and is exposed to an outside; and
    an annular extension extending radially from an outer perimeter of a distal end of each adsorbing cup.

2. The dry adhesive patch of claim 1, wherein a hydrogel is received in the hemi-spherical hole of the adsorbing cup.

3. The dry adhesive patch of claim 2, wherein the hydrogel contains a hydrophilic functional group.

4. The dry adhesive patch of claim 2, wherein the hydrogel includes at least one selected from a group consisting of polyacrylamide, polyaniline, polyethylene glycol, and alginate.

5. The dry adhesive patch of claim 2, wherein the hydrogel has a porous chain network shape.

6. The dry adhesive patch of claim 2, wherein the hydrogel occupies 70% or greater of a volume of the hole defined in the adsorbing cup.

7. The dry adhesive patch of claim 2, wherein a diameter of the hemi-spherical hole defined in the adsorbing cup is smaller than a diameter of the adsorbing cup.

8. The dry adhesive patch of claim 2, wherein the dry adhesive patch containing the hydrogel exhibits higher adhesive force in wet and dry environments than the dry adhesive patch free of the hydrogel exhibits.

9. The dry adhesive patch of claim 1, wherein the dry adhesive patch having the annular extension exhibits higher adhesive force in wet and dry environments than the dry adhesive patch free of the annular extension exhibits.

10. A biological skin surface patch for capturing a body fluid, the patch including the dry adhesive patch of claim 2.

11. The biological skin surface patch of claim 10, wherein the biological skin surface patch further comprises:
    a first electrode outwardly extending from the hole of the adsorbing cup;
    a second electrode outwardly extending from the hole of the adsorbing cup, wherein the second electrode is spaced from the second electrode, wherein each of the first and second electrodes is in contact with the hydrogel; and
    an electrical signal measuring unit connected to the first and second electrodes to measure an electrical signal to analyze a body fluid captured in the hydrogel.

12. A method for manufacturing a dry adhesive patch, the method comprising:
    providing a mold substrate having embossed engraved patterns defined therein;
    providing a film having a polymer precursor solution applied thereon;
    placing the film on the mold substrate such that air is trapped in the embossed engraved patterns;
    pressing a back face of the film to convert the trapped air to an air bubble;
    curing the polymer precursor solution;
    separating the cured polymer precursor from the mold substrate to form embossed pillars; and
    stamping a sticky polymer onto a top face of each of the embossed pillars to form an adsorbing cup having an annular extension extending radially from a distal end thereof.

13. The method of claim 12, wherein the method further comprises filling a hydrogel into the adsorbing cup.

* * * * *